(12) United States Patent
Reevell

(10) Patent No.: US 11,896,758 B2
(45) Date of Patent: *Feb. 13, 2024

(54) E-VAPING DEVICE WITH FIRST-TYPE CONSUMABLE AND SECOND-TYPE CONSUMABLE

(71) Applicant: Altria Client Services LLC, Richmond, VA (US)

(72) Inventor: Tony Reevell, London (GB)

(73) Assignee: Altria Client Services LLC, Richmond, VA (US)

( * ) Notice: Subject to any disclaimer, the term of this patent is extended or adjusted under 35 U.S.C. 154(b) by 663 days.

This patent is subject to a terminal disclaimer.

(21) Appl. No.: 17/003,084

(22) Filed: Aug. 26, 2020

(65) Prior Publication Data

US 2020/0390987 A1    Dec. 17, 2020

Related U.S. Application Data

(60) Division of application No. 15/885,116, filed on Jan. 31, 2018, now Pat. No. 10,758,686, which is a
(Continued)

(30) Foreign Application Priority Data

Jan. 31, 2017    (EP) ..................................... 17153929

(51) Int. Cl.
*A24F 47/00*    (2020.01)
*A61M 11/04*    (2006.01)
(Continued)

(52) U.S. Cl.
CPC ........... *A61M 11/042* (2014.02); *A24F 40/30* (2020.01); *A24F 40/40* (2020.01); *A24F 40/42* (2020.01);
(Continued)

(58) Field of Classification Search
None
See application file for complete search history.

(56) References Cited

U.S. PATENT DOCUMENTS 2,592,369 A    4/1952    Young et al.
4,655,229 A    4/1987    Sensabaugh, Jr. et al.
(Continued)

FOREIGN PATENT DOCUMENTS

CN    203563687 U    4/2014
CN    106102490 A    11/2016
(Continued)

OTHER PUBLICATIONS

Office Action dated Dec. 16, 2022, issued in corresponding Korean Patent Application No. 2019-7019750.
(Continued)

*Primary Examiner* — Joseph M. Pelham
(74) *Attorney, Agent, or Firm* — Harness, Dickey & Pierce, P.L.C.

(57) ABSTRACT

The e-vaping device includes a first housing, a chamber defined within the first housing, a first structure and a second structure that interface with the chamber, the first structure is configured to accept at least one first-type consumable within the chamber and the second structure is configured to receive at least one second-type consumable within the chamber.

21 Claims, 7 Drawing Sheets

Related U.S. Application Data continuation of application No. PCT/EP2017/084193, filed on Dec. 21, 2017.

(51) Int. Cl.

| | | |
|---|---|---|
| *A61M 15/00* | (2006.01) | |
| *A61M 15/06* | (2006.01) | |
| *A24F 40/42* | (2020.01) | |
| *A24F 40/30* | (2020.01) | |
| *A24F 40/40* | (2020.01) | |
| *A24F 40/53* | (2020.01) | |
| *A24F 40/10* | (2020.01) | |
| *A24F 40/20* | (2020.01) | |

(52) U.S. Cl.
CPC .......... *A24F 40/53* (2020.01); *A61M 15/003* (2014.02); *A61M 15/0036* (2014.02); *A61M 15/06* (2013.01); *A24F 40/10* (2020.01); *A24F 40/20* (2020.01); *A61M 15/0003* (2014.02); *A61M 15/004* (2014.02); *A61M 15/0021* (2014.02); *A61M 15/0031* (2014.02); *A61M 15/0041* (2014.02); *A61M 2202/04* (2013.01); *A61M 2202/064* (2013.01); *A61M 2205/121* (2013.01); *A61M 2205/13* (2013.01); *A61M 2205/14* (2013.01); *A61M 2205/27* (2013.01); *A61M 2205/3317* (2013.01); *A61M 2205/3653* (2013.01); *A61M 2205/6018* (2013.01); *A61M 2205/6027* (2013.01); *A61M 2205/6036* (2013.01); *A61M 2205/6045* (2013.01); *A61M 2205/8206* (2013.01)

(56) References Cited

U.S. PATENT DOCUMENTS

| | | | | |
|---|---|---|---|---|
| 10,368,581 | B2 * | 8/2019 | Rostami | A61M 11/042 |
| 11,197,501 | B1 * | 12/2021 | Washington | H05B 1/0227 |
| 11,589,429 | B2 * | 2/2023 | Reevell | H01C 17/24 |
| 2002/0134374 | A1 | 9/2002 | Loeffler et al. | |
| 2012/0048266 | A1 | 3/2012 | Alelov | |
| 2013/0014772 | A1 | 1/2013 | Liu | |
| 2013/0333700 | A1 | 12/2013 | Buchberger | |
| 2014/0060556 | A1 | 3/2014 | Liu | |
| 2015/0090253 | A1 | 4/2015 | Farrow | |
| 2015/0296889 | A1 | 10/2015 | Liu | |
| 2016/0050976 | A1 | 2/2016 | Righetti et al. | |
| 2016/0073695 | A1 | 3/2016 | Sears et al. | |
| 2016/0089508 | A1 | 3/2016 | Smith et al. | |
| 2016/0345629 | A1 | 12/2016 | Mironov | |
| 2017/0258138 | A1 | 9/2017 | Rostami et al. | |
| 2017/0258140 | A1 * | 9/2017 | Rostami | A24F 40/30 |
| 2018/0027882 | A1 | 2/2018 | Hepworth et al. | |
| 2018/0132534 | A1 | 5/2018 | Reevell | |
| 2018/0132535 | A1 | 5/2018 | Reevell | |
| 2018/0168228 | A1 | 6/2018 | Reevell | |
| 2018/0168230 | A1 | 6/2018 | Reevell | |
| 2018/0168231 | A1 | 6/2018 | Reevell | |
| 2018/0169355 | A1 | 6/2018 | Reevell | |
| 2018/0213847 | A1 * | 8/2018 | Reevell | A24F 40/485 |
| 2018/0263286 | A1 * | 9/2018 | Reevell | A61M 15/0003 |
| 2018/0289069 | A1 * | 10/2018 | Reevell | H02J 7/34 |
| 2018/0338531 | A1 | 11/2018 | Reevell | |
| 2019/0142071 | A1 | 5/2019 | Seok | |
| 2020/0268057 | A1 * | 8/2020 | Sahin | A61M 15/06 |
| 2021/0084964 | A1 * | 3/2021 | Matsumoto | A24F 40/46 |
| 2022/0160032 | A1 * | 5/2022 | Glaser | A24F 40/57 |

FOREIGN PATENT DOCUMENTS

| | | | |
|---|---|---|---|
| CN | 106163309 | A | 11/2016 |
| CN | 106255430 | A | 12/2016 |
| CN | 106535681 | A | 3/2017 |
| CN | 106659247 | A | 5/2017 |
| CN | 108851219 | A | 11/2018 |
| GB | 2534855 | A | 8/2016 |
| JP | 2015/198985 | A | 11/2015 |
| KR | 200465795 | Y1 | 3/2013 |
| KR | 2016/0008510 | A | 1/2016 |
| RU | 2135054 | C1 | 8/1999 |
| WO | WO-2014/166034 | A1 | 10/2014 |
| WO | WO-2015/0179388 | A1 | 11/2015 |
| WO | WO-2016/005602 | A1 | 1/2016 |
| WO | WO-2016/107768 | A1 | 7/2016 |

OTHER PUBLICATIONS

Office Action dated Nov. 24, 2021, issued in corresponding Chinese Patent Application No. 201780082385.2.
Decision to Grant dated Jan. 4, 2022, issued in corresponding Japanese Patent Application No. 2019-539879.
Russian Decision to Grant and Search Report dated Apr. 20, 2021 issued in corresponding Russian Patent Application 2019127305.
Kazak Decision to Grant dated Sep. 23, 2020 issued in corresponding Kazakhstan Patent Application No. 2019/0600.1.
Notice of Allowance dated Jun. 21, 2023, issued in corresponding Korean Patent Application No. 2019-7019750.
"British American to test tobacco/e-cigarette hybrid" http://www.reuters.com/article/us-brit-am-tobacco-products-idUSKCNOT71U020151118 <https://protect-us.mimecast.com/s/U4IPCxkVn8Cr35Gc7yYhQ>.
"HVS-Hybrid Vaping System", http://jinjiatech.com/PRODUCTS/Heat/91 <https://protect-us.mimecast.com/s/4g5zCyP607C9RPjSnMh3j>.
European Search Report for European Patent Application No. 17153929.9 dated Sep. 13, 2017.
International Search Report and Written Opinion dated Apr. 19, 2018 for related PCT Application No. PCT/EP2017/084193.
Written Opinion dated Jan. 4, 2019 in corresponding PCT Application No. PCT/EP2017/084193.
Notification concerning informal communications with the Applicant, issued Apr. 23, 2019.
International Preliminary Report on Patentability dated May 17, 2019 in PCT/EP2017/084193.

* cited by examiner

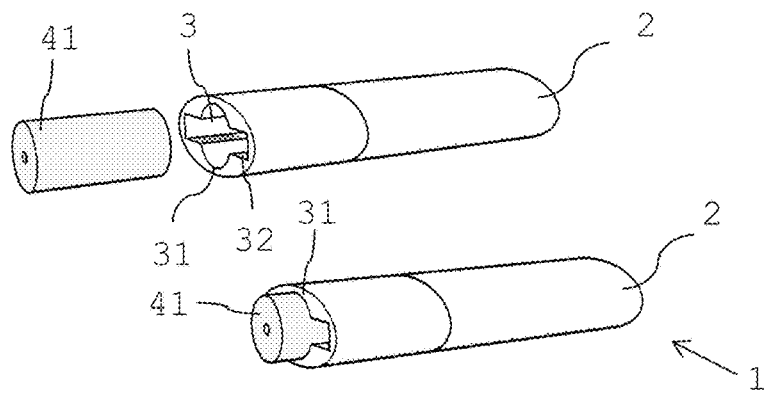
Fig. 1
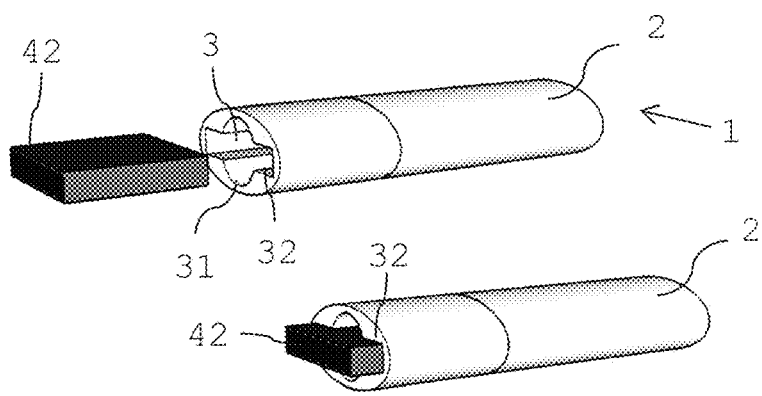
Fig. 2
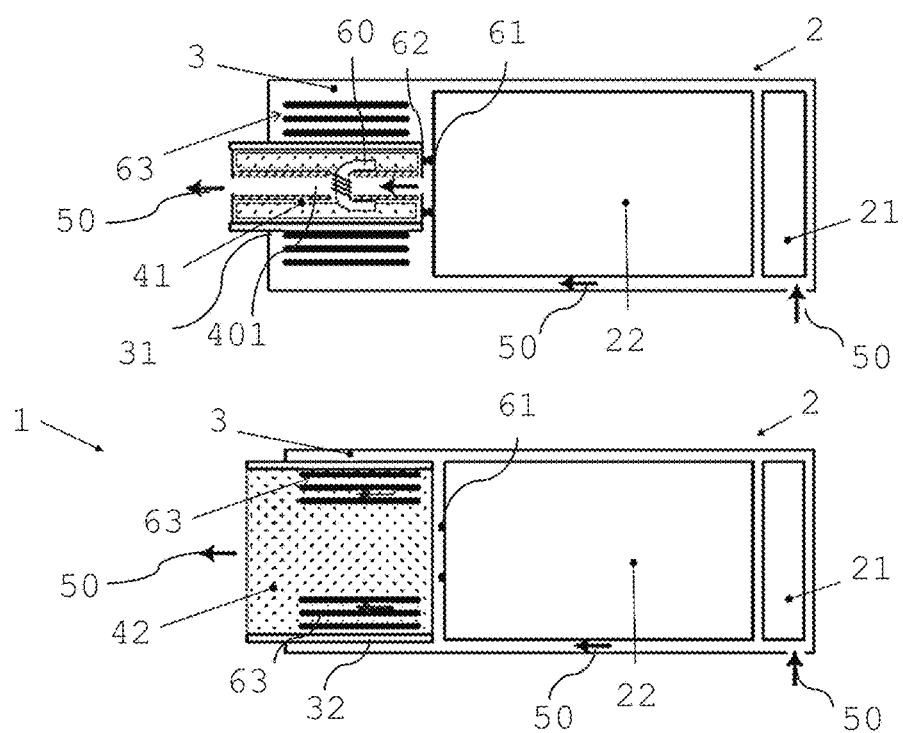
Fig. 3
Fig. 4

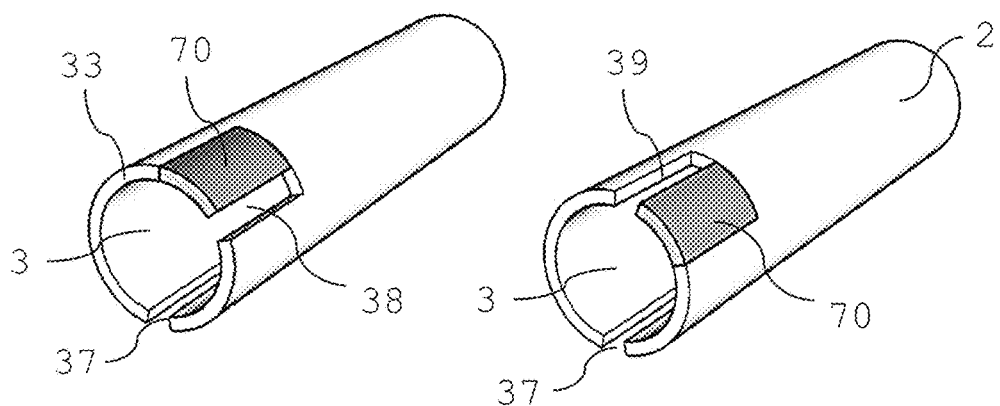
Fig. 16    Fig. 17
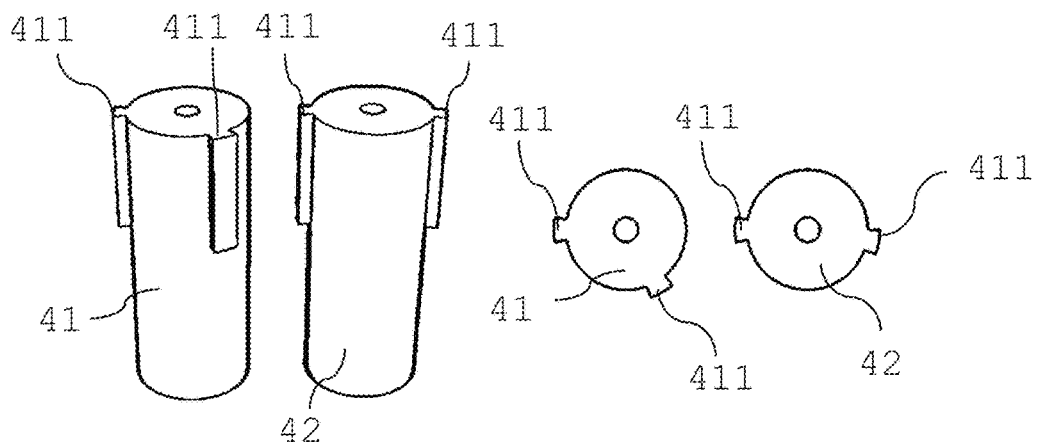
Fig. 18
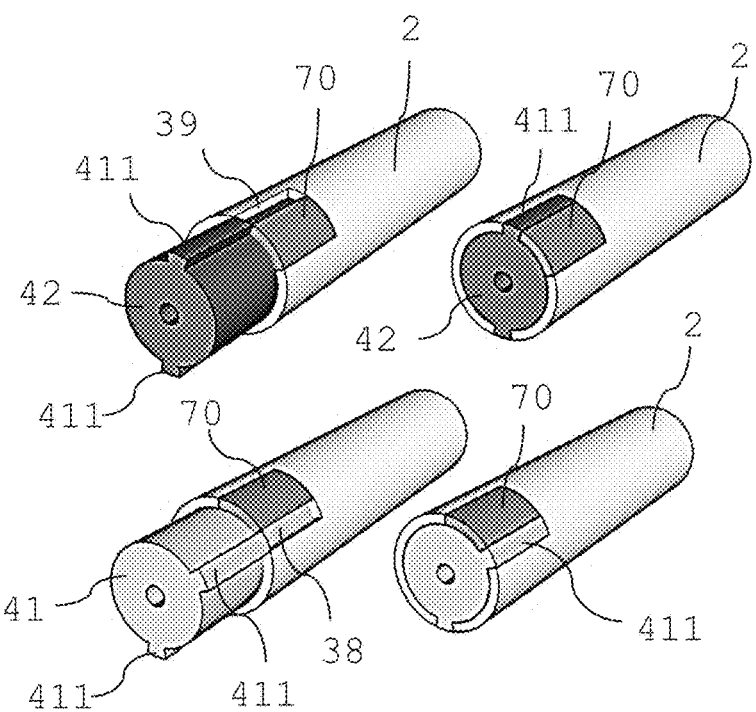
Fig. 19
Fig. 20

E-VAPING DEVICE WITH FIRST-TYPE CONSUMABLE AND SECOND-TYPE CONSUMABLE

CROSS-REFERENCE TO RELATED APPLICATION

This application is a divisional of U.S. application Ser. No. 15/885,116, filed Jan. 31, 2018, which is a continuation of and claims priority to international application number PCT/EP2017/084193, filed on Dec. 21, 2017, and further claims priority under 35 USC § 119 to European patent application number 17153929.9, filed Jan. 31, 2017, the entire contents of each of which are incorporated herein by reference.

FIELD

Example embodiments relate to an e-vaping device with a first-type consumable and second-type consumable.

DESCRIPTION OF RELATED ART

Aerosol-generating (vapor-generating) devices are known to use a liquid to be evaporated or a tobacco material to be heated. In some systems, the evaporation of a liquid is combined with heating tobacco.

SUMMARY

At least one example embodiment relates to an aerosol-generating (electronic-vaping, or e-vaping) device.

In one embodiment, the aerosol-generating device includes a device housing; a receiving chamber defined within the device housing, the receiving chamber being configured to receive at least a first-type consumable and a second-type consumable, the receiving chamber including a first structure for receiving the first-type consumable and a second structure for receiving the second-type consumable; a structure selector for selecting between the first structure and the second structure, the first and second structures differing in at least one of a shape, a size and a position within the receiving chamber; and an aerosolization system associated with at least a portion of the receiving chamber, wherein the receiving chamber is configured to prevent an insertion of more than one consumable into the receiving chamber.

In one embodiment, the aerosol-generating device further includes, a detection system configured to detect a presence of the first-type consumable and the second-type consumable that has been inserted into the receiving chamber, wherein the aerosolization system is configured to function to generate an aerosol using both the first-type consumable and the second type consumable following their insertion into the receiving chamber.

In one embodiment, the first and the second structures are in the receiving chamber, the first and the second structures being at least one of positioned in a receiving chamber wall of the receiving chamber and forming portions of the receiving chamber wall.

In one embodiment, the receiving chamber includes a recess arranged in a bottom wall of the receiving chamber to receive at least one of the first-type consumable and the second-type consumable.

In one embodiment, at least one of the first structure and the second structure is selectable by moving and thereby positioning the structure selector in the receiving chamber.

In one embodiment, the structure selector is part of a receiving chamber side wall, the structure selector including different positions that correspond to notches in the receiving chamber side wall that are arranged at different locations.

In one embodiment, the structure selector includes a movable receiving chamber side wall portion, wherein the different positions of the structure selector correspond to different diameters of the receiving chamber.

In one embodiment, the receiving chamber includes at least one of a heating element and electrical contacts connectable to an external heating element, the external heating element being in at least one of the first-type consumable and the second-type consumable.

In one embodiment, the receiving chamber includes the heating element for heating the first-type consumable and includes the electrical contacts that are connectable to the external heating element in the second-type consumable.

In one embodiment, the receiving chamber further includes a third structure for receiving a third-type consumable, the third structure differing in at least one of a shape, a size and a position in the receiving chamber as compared to the first structure and the second structure.

In one embodiment, the receiving chamber is arranged in a hinged portion of the device housing, the hinged portion being movable between a closed configuration where the receiving chamber is not accessible and an open configuration where the receiving chamber is accessible for insertion of the first-type consumable and the second-type consumable.

At least another example embodiment relates to an aerosol-generating system.

In one embodiment, the aerosol-generating system includes an aerosol-generating device, the aerosol-generating device including, a device housing, a receiving chamber defined within the device housing, the receiving chamber being configured to receive at least a first-type consumable and a second-type consumable, the receiving chamber including a first structure for receiving the first-type consumable and a second structure for receiving the second-type consumable, a structure selector for selecting between the first structure and the second structure, the first and second structures differing in at least one of a shape, a size and a position within the receiving chamber, and an aerosolization system associated with at least a portion of the receiving chamber, the receiving chamber being configured to prevent an insertion of more than one consumable into the receiving chamber, wherein the first-type consumable is arranged in the receiving chamber with portions of a first shape of the first-type consumable correlating to the first structure, and the second-type consumable is arranged in the receiving chamber with portions of a second shape of the second-type consumable correlating to the second structure.

In one embodiment, a first portion of the receiving chamber corresponds to a second portion of a first outer periphery of the first-type consumable, and a second portion of the receiving chamber corresponds to a third portion of a second outer periphery of the second-type consumable.

In one embodiment, the first-type consumable and the second-type consumable includes at least two laterally extending lugs, wherein the at least two lugs of the first-type consumable and the at least two lugs of the second-type consumable differ in at least one of a circumferential arrangement and a shape, and an opening portion of the receiving chamber includes notches having a shape and distribution along the opening portion that correspond to the shape and the circumferential arrangement of the lugs of the first-type consumable and the second-type consumable.

In one embodiment, the aerosol-generating device further includes, a consumable insert configured to be inserted into the receiving chamber, the insert including a cylindrical portion and two oppositely arranged flaps depending from the cylindrical portion.

In one embodiment, the consumable insert includes an opening protection, the opening protection being at least one of a sealing foil sealing an opening of the consumable insert, a break-off tab connected to the consumable insert, and a sealed sachet containing the consumable insert.

BRIEF DESCRIPTION OF THE DRAWINGS

Features described in relation to one example embodiment may equally be applied to other example embodiments.

Example embodiments will now be described with reference to the following drawings.

FIG. 1 illustrates an aerosol-generating device with a first-type consumable, in accordance with an example embodiment;

FIG. 2 illustrates the aerosol-generating device of FIG. 1 with a second-type consumable, in accordance with an example embodiment;

FIG. 3 illustrates a cross-sectional view of the devices shown in FIGS. 1 and 2, in accordance with an example embodiment;

FIG. 4 illustrates a cross-sectional view of the devices shown in FIGS. 1 and 2, in accordance with an example embodiment;

FIG. 16 illustrates a device housing including a structure selector with two different positions, in accordance with an example embodiment;

FIG. 17 illustrates a device housing including a structure selector with two different positions, in accordance with an example embodiment;

FIG. 18 illustrates two consumables to be used and accommodated in the device housing shown in FIGS. 19 and 20, in order accordance with an example embodiment;

FIG. 19 illustrates a device housing, in accordance with an example embodiment;

FIG. 20 illustrates a device housing, in accordance with an example embodiment;

DETAILED DESCRIPTION

Figure 5:
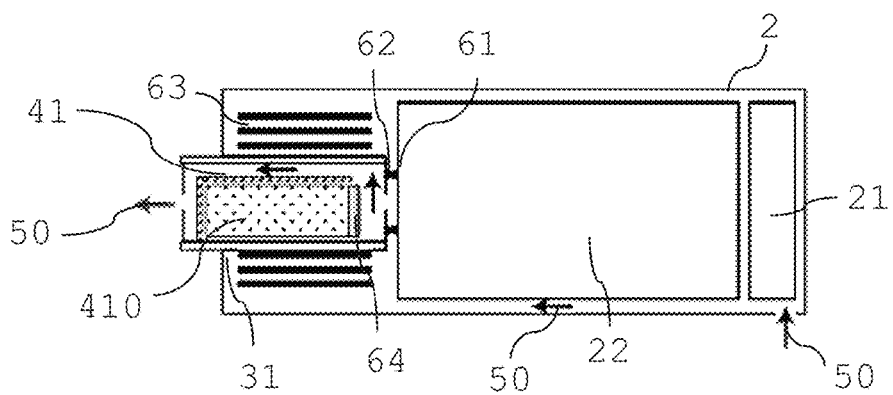
FIG. 5 illustrates a cross-sectional view of the devices shown in FIGS. 1 and 2, in accordance with an example embodiment.

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings set forth herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these example embodiments should not be construed as limited to the particular shapes of regions illustrated herein, but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of this disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

In the following description, illustrative embodiments may be described with reference to acts and symbolic representations of operations (e.g., in the form of flow charts, flow diagrams, data flow diagrams, structure diagrams, block diagrams, etc.) that may be implemented as program modules or functional processes including routines, programs, objects, components, data structures, etc., that perform particular tasks or implement particular abstract data types. The operations be implemented using existing hardware in existing electronic systems, such as one or more microprocessors, Central Processing Units (CPUs), digital signal processors (DSPs), application-specific-integrated-circuits (ASICs), SoCs, field programmable gate arrays (FPGAs), computers, or the like.

Further, one or more example embodiments may be (or include) hardware, firmware, hardware executing software, or any combination thereof. Such hardware may include one or more microprocessors, CPUs, SoCs, DSPs, ASICs, FPGAs, computers, or the like, configured as special purpose machines to perform the functions described herein as well as any other well-known functions of these elements. In at least some cases, CPUs, SoCs, DSPs, ASICs and FPGAs may generally be referred to as processing circuits, processors and/or microprocessors.

Although processes may be described with regard to sequential operations, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

General Methodology:

Example embodiments include aerosol-generating systems that provide a choice of using different consumables.

Example embodiments include an aerosol-generating device with a device housing including a receiving chamber adapted to receive any one of a first-type consumable and a second-type consumable. A first-type consumable and a second-type consumable may differ in at least one of shape or size. The receiving chamber includes a first structure for receiving a first-type consumable and includes a second structure for receiving a second-type consumable or includes a structure selector for selecting between a first structure and a second structure. The first and second structures differ in at least one of shape, size or position in the receiving chamber.

The device further includes an aerosolization system associated with at least a portion of the receiving chamber. The aerosolization system is configured to cooperate with any one of a first-type or second type consumable once inserted into the receiving chamber, for generating aerosol. The aerosolization system may include a power source and a heating element for heating a consumable inserted into the receiving chamber. The aerosolization device may also include electrical contacts arranged in the receiving chamber for being connected and providing power to a heating element present in a consumable for heating the consumable. The aerosolization system may also include a controller for controlling a power supply to a heating element or for controlling an aerosolization process.

The receiving chamber may be configured such that when a consumable is received in the receiving chamber a further consumable is prevented from being received in the receiving chamber. This may mean that the receiving chamber is configured so that it can only receive one consumable at a time. That is, the receiving chamber may be configured so that it can only receive single, or individual consumables, and cannot receive a plurality of consumables. For example, in such an arrangement, the consumable that has already been received in the receiving chamber can itself be held in the receiving chamber in a way that prevents a further consumable from being received in the receiving chamber. Alternatively or additionally, the receiving chamber may be arranged such that once it has received a consumable, structure is activated for preventing the receiving chamber from receiving one or more further consumables.

The device may also include a detection system configured to detect the presence of a first-type consumable or of a second-type consumable inserted into the receiving chamber. The first-type or second-type consumable is accordingly correlated with, for example received in, the first structure or in the second structure of the receiving chamber. In an embodiment, the detection system recognizes the type of consumable such that operation of the device, in particular a heating process is tailored and optimized to the specific type of consumable.

As explained in more detail below, in some embodiments, the shape of the consumable which is inserted into the receiving chamber may allow the device to recognise which type of consumable has been received in the receiving chamber. The device may use this recognition to then determine how to process the consumable. For example, the device may use this recognition to then determine one or both of: which heating elements to activate, and which temperature program to use for the consumable. In particular, the device may be configured to use different heaters for different types of detected consumables received in the receiving chamber. The different heaters may be different types of heaters provided in the device or may be different heating elements of a heater.

All structures in the receiving chamber corresponding to different types of consumables may be present in the receiving chamber at all times. By this, any type of consumable intended to be used in combination with the device may be inserted into the receiving chamber. Shape or size of the consumables correspond to the respective structures in the receiving chamber. In an embodiment, the consumable or a portion of the consumable forms a form fit with the corresponding structure of the receiving chamber.

For example, the receiving chamber may include, as a first structure, a cylindrical portion adapted for receiving a cylindrically shaped consumable. The receiving chamber may include, as a second structure, a rectangular portion extending though and over the cylindrical portion. The rectangular portion is adapted for receiving a rectangular shaped consumable.

Structures of the receiving chamber may also be designed to be selectable at the time of use of the device by the structure selector. Thus, structures may be foreseen in the receiving chamber but are created or provided only upon use of the device and after the consumable to be consumed has been selected. A structure selector is positioned accordingly such as to create the respective structure in the receiving chamber to correspond to the selected type of consumable.

Such selection or provision of structures at the time of use provides the advantage that the adaption of the device may, for example, directly be used as a detection system. For example, the structure selector, for example embodied in the form of a switch, may provide a first structure in a receiving chamber wall when in a first position and may provide a second structure at a different position in the receiving chamber wall when in a second position. The positions of the structure selector then directly correspond to a first-type consumable and a second-type consumable. The first and the second structures may be structures in a receiving chamber wall or may form portions of a receiving chamber wall. For example, the first and second structures may be structures or form portions of a receiving chamber bottom wall or of a receiving chamber side wall.

For example, the receiving chamber may include a recess arranged in a bottom wall of the receiving chamber to receive any one of a first-type consumable or a second-type consumable in the recess. In an embodiment, the form and size of the recess corresponds to the form and size of a bottom portion of one type of consumable.

The entire bottom wall of the receiving chamber may correspond to another type of consumable.

The receiving chamber may have a shape and size corresponding to the shape and size of another type of consumable. For example, the receiving chamber may have the form of a cylinder. The recess may then be a circular, for example centrally arranged recess having a smaller diameter than the bottom wall of the receiving chamber. Thus, in such an embodiment, the receiving chamber of the device is adapted to receive two cylindrically shaped consumables having different diameters, a smaller and a larger diameter.

The recess may include a puncturing member that extends from the recess into the direction of the receiving chamber. Such a puncturing member may adapt the device to be usable in combination with consumables requiring puncturing. For example, a cartridge or capsule may be punctured to gain access to an aerosol-forming substrate or a powder in the cartridge or capsule. The puncturing member may be open such as to allow an airflow to pass through the puncturing member into or through the punctured consumable. In an embodiment, a puncturing member has a height which is the same or smaller than a depth of a recess such that the puncturing member does not extend over the recess. By this, another type of consumable, not requiring puncturing, inserted into the receiving chamber but not inserted into the recess is kept unaffected by the puncturing member.

The structures of the receiving chamber may, for example, be one or several notches in an opening portion of a receiving chamber side wall. The arrangement and possibly also the shape or sizes of the notches correspond to specific types of consumable. For example, the opening portion of the receiving chamber side wall may include two oppositely arranged notches corresponding to a consumable having two opposite arranged lugs extending from the periphery of the consumable. The opening portion may have a third notch arranged in between the first and second notches. Accordingly, a second type of consumable may comprise two lugs extending from the periphery of the consumable, however which lugs are not oppositely arranged but at an angle smaller than 180 degree.

Notches in an opening portion of the receiving chamber side wall are well suited for being selectable upon use of the device by a structure selector.

In an example embodiment, the first structure or the second structure or both the first and the second structures of the device may be selectable by moving and thereby positioning the structure selector in the receiving chamber. The structure selector may be a movable part of the receiving chamber side wall. Different positions of the structure selector then correspond to notches such as for example slits or grooves, in the receiving chamber side wall arranged at different positions in the receiving chamber side wall.

The structure selector may also be a removable part of the chamber side wall. In the mounted position of the structure selector, the receiving chamber is adapted to receive at least a first-type consumable. In the removed position of the structure selector, the receiving chamber side wall includes an opening area. By this, the receiving chamber may be adapted to receive a second-type consumable. In an embodiment, in the removed position of the structure selector the device is disabled and use of the device is prevented. In an embodiment, a removable structure selector may be remounted such as to be in a mounted position again.

The structure selector may be a combined movable and removable part of the receiving chamber. In such embodiments, different positions of the structure selector may create different recesses in the receiving chamber side wall, while the removed structure selector may correspond to a further position of the structure selector or to a disabling function of the device.

The structure selector may also be a movable receiving chamber wall portion, wherein different positions of the structure selector correspond to different diameters of the receiving chamber. The receiving chamber may include at least one heating element for heating a consumable accommodated in the receiving chamber. In an embodiment, the heating element is an electrical heating element such as, for example, an induction coil or a resistively heatable heating element.

The receiving chamber may include electrical contacts connectable to an external heating element of a consumable for heating said consumable accommodated in the receiving chamber.

In an embodiment, the receiving chamber includes a heating element for heating a first-type consumable and comprises electrical contacts for being connected to an external heating element of a second-type consumable.

The receiving chamber may include a heating element or different heating elements and electrical contacts for a heating element per type of consumable. By this, the device is adapted to be used together with differently shaped consumables independent of the way they are heated. For example, cylindrically shaped consumables include a liquid substrate and a heating element, for example a coil surrounding a wick, may be used in a receiving chamber in combination with the same structures of the receiving chamber than, for example, an inductively heatable cylindrical tobacco plug. In the first case, power from a power source in the device is delivered to the heating element of the liquid containing consumable via electrical contacts in the receiving chamber. In the latter case, an induction coil, for example arranged in the receiving chamber side wall, induces energy in a susceptor material in the tobacco plug.

The receiving chamber of the aerosol-generating device may include a third structure for receiving a third-type consumable. The third structure differs in at least one of shape, size or position in the receiving chamber from the first structure and from the second structure. The receiving chamber may be provided with a third structure in the receiving chamber wall or the third structure may form portions of the receiving chamber wall. For example, the bottom wall of the receiving chamber may be provided with two recesses, for example to concentrically arranged recesses. Each of the recesses may, for example, be arranged in a staggered manner in the bottom of the receiving chamber. One recess may then correspond to a first-type consumable, the second recess may then correspond to a second-type consumable and the entire bottom wall of the receiving chamber may correspond to a third-type consumable.

One or several further notches may be provided in an opening portion of the receiving chamber side wall.

A structure selector may be designed to be movable to a third position selecting the third structure. For example, movement of the structure selector may create a further notch at a different position or of a different shape, or both at a different position and of a different shape, in the opening portion of the receiving chamber side wall.

In an embodiment, a third-type consumable differs from the first-type consumable and from the second-type consumable at least by its shape or size.

Access to the receiving chamber for insertion of a consumable may always be available. In such embodiments, the consumable may be directly contacted when the device is used. The consumable may extend from the receiving chamber to allow such contacting.

Access to the receiving chamber may, for example, be gained by a disassembly of the device, for example by removal of a mouthpiece that is removably connected to the device housing.

The receiving chamber may, for example, also be arranged in a hinged portion of the device housing. The hinged portion may be movable by the hinge between a closed configuration where the receiving chamber is not accessible and an open configuration where the receiving chamber is accessible for insertion of the first-type consumable or the second-type consumable or any further type of consumables.

The hinged portion is in the closed configuration aligned with the rest of the device housing, for example arranged in a same plane as the rest of the housing. In the open configuration, the hinged portion is tilted and extends from said plane.

In an example embodiment, there is also provided an aerosol-generating system including an aerosol-generating device, described herein. In the system, a first-type consumable is arranged in the receiving chamber with portions of the shape of the first-type consumable correlating to a first structure in the receiving chamber. Alternatively, a second-type consumable is arranged in the receiving chamber with portions of the shape of the second-type consumable correlating to a second structure in the receiving chamber.

In an embodiment, a portion of the receiving chamber corresponds solely to a portion of the outer periphery of the first-type consumable. In an embodiment, another portion of the receiving chamber corresponds solely to a portion of the outer periphery of the second-type consumable. Yet a further portion of the receiving chamber may correspond solely to a portion of the outer periphery of a third-type or further-type consumable. In an embodiment, the portions of the receiving chamber forms a form fit with the respective peripheral portions of the respective consumables. The portions of the receiving chamber corresponding solely to one type of consumable may be portions of a bottom wall or of a side wall of the receiving chamber.

In some embodiments of the system, each of the consumables to be used in the system includes at least two laterally or radially extending lugs. The at least two lugs of the first-type consumable and the at least two lugs of the second-type consumable and possibly the at least two lugs of a third-type or further-type consumable differ in at least one of circumferential arrangement or shape of the lugs. An opening portion of the receiving chamber includes notches having a shape and distribution along the opening portion corresponding to or selectable to correspond (via a structure selector of the receiving chamber) to the shape and distribution of the lugs of either the first-type consumable or of the second-type consumable or of the third-type or further-type consumable.

Further elements and advantages of the system have been described relating to the aerosol-generating device and will not be repeated.

Various types of consumables may be used or may be determined to be usable with the aerosol-generating device and in the aerosol-generating system, according to example embodiments.

Examples of such consumables are liquid containing cartridges or tank systems including or excluding an integrated heating element such as for example a cartridge, or a combined cartridge and atomizer; solid substrate containing consumables such as for example tobacco containing plugs or plates, solid substrate containing capsules, wherein the solid substrate may be tobacco material, homogenized tobacco material, substrate in powder form, vaporizable wax, tobacco sheets that are gathered or crimped.

In the system according to example embodiments, a first-type consumable may include a liquid aerosol-forming substrate, and a second-type consumable may include a solid substrate. If a third-type consumable is available for use in the system, the third type consumable may use a different substrate or use of a different method for releasing substances from the consumable. For example, a third-type consumable may include a substrate in powdery form or may be a non-heated tobacco substrate.

Accordingly, the receiving chamber of the device may include a heating element for heating the first-type consumable and may include electrical contacts connected to the external heating element of the second-type consumable when the second type consumable is accommodated in the receiving chamber. The system may further include either a heating element or electrical contacts for an external heating element for heating a third-type consumable.

According to example embodiments, there is further provided a consumable insert. The consumable insert is adapted for being inserted into a receiving chamber of an aerosol-generating device, as described herein. The insert includes a cylindrical portion and two oppositely arranged flaps depending from the cylindrical portion. The cylindrical portion is associated to a first-type consumable, while the two oppositely arranged flaps are associated to a second-type consumable. In an embodiment, the flaps extend radially in opposite directions from the cylindrical portion. The first-type consumable is directed to a consumable having a substantially cylindrical shape. The second-type consumable is directed to a consumable having a substantially flat rectangular shape.

The term "depending" is used herein to describe a physical connection between two elements of an insert. In more detail, the term "depending" is used to indicate that there is a material continuity between two elements, such as cylindrical portion and flap of an insert. A flap and cylindrical portion may be manufactured in one piece, for example integrally molded or integrally deep-drawn. The flaps may also be attached to the cylindrical portion, for example by sealing or gluing.

The consumable insert includes an opening for insertion and access of an aerosol-forming substrate.

In an embodiment, the cylindrical portion is a hollow cylinder. In an embodiment, a bottom or distal end of the cylinder is closed and forms part of the cylinder.

In an embodiment, an aerosol-forming substrate is provided in the cylindrical portion.

The flaps may contain no aerosol-forming substrate or may contain aerosol-forming substrate. For example, the flaps may serve as positioning structure or may contain a liquid aerosol-forming substrate or may be a combination thereof.

In an embodiment, no aerosol-forming substrate is provided in the flaps.

The flaps may facilitate an insertion of the consumable insert in a receiving chamber of an aerosol-generating device. The flaps may also serve for a positioning of the insert in the receiving chamber defining two positions of the insert. The positions may, for example, be correlated to the position of a heating element or to electrical contacts for a heating element such as to optimize a heating of an aerosol-forming substrate in the cylindrical portion of the consumable insert. This may particularly be advantageous when using consumables including a susceptor to be arranged in a device including an inductor such as an induction coil. A precise position adjustment of the susceptor relative to the inductor is thereby facilitated.

The flaps may also serve as electrical contacts for a heating element arranged at the cylindrical portion. For example, the flaps may be made for electrically conductive material or conductive paths or wires may be provided on the flaps as electrical contacts for a resistive or inductive heating element in the cylindrical portion.

When the flaps serve as liquid aerosol-forming substrate reservoir, the consumable insert is a hybrid consumable providing two different substrates. In an embodiment, a tobacco substrate is combined with a liquid substrate, for example providing at least one of nicotine and flavor.

In an embodiment, the consumable insert includes an opening protection to protect an aerosol-forming substrate provided in the insert, and may be provided in the cylindrical portion of the insert. The opening protection may extend over a proximal end of the cylindrical portion only. In an embodiment, the opening protection extends over the entire proximal end of the insert, that is, over the proximal end of the cylindrical portion as well as of the two flaps.

The opening protection may, for example be a sealing foil sealing an opening of the insert, for example the proximal end of the cylindrical portion.

The opening protection may, for example be a break-off tab connected to the insert. Such a break-off tab may be broken away providing access to an aerosol-generating substrate in the insert.

The opening protection may, for example be a sealed sachet where the consumable assembly insert is packed in.

The opening protection may also be a combination of the above mentioned examples of opening protections. For example, a consumable insert may include a sealed opening and may be packed in a sealed sachet.

Structural Embodiments:

In the drawings, the same reference numbers are used for the same or similar elements.

FIG. 1 illustrates an aerosol-generating (also referred to as a "vapor-generating") device 1 including a device housing 2 and a receiving chamber 3 provided in the device housing 2, in accordance with an example embodiment. The receiving chamber 3 may have the form of a hollow cylinder 31 combined with a hollow cuboid 32. The receiving chamber 3 is centro-symmetrically arranged in the device housing 2. A first-type consumable 41 in the form of a cylinder having a circular cross section is inserted into and accommodated in the cylinder part 31 of the receiving chamber 3. In FIG. 2, a second-type consumable 42 that may be in the form of a cuboid having a rectangular cross section is inserted into the cuboid part 32 of the receiving chamber 3 of the same device 1.

Both consumables 41,42 are not completely inserted in the receiving chamber 3. They extend from the receiving chamber 3 to simplify removal of the consumables 41,42 after use.

FIGS. 3 and 4 illustrate cross-sectional views of the aerosol-generating device 1 of FIGS. 1 and 2, in accordance with an example embodiment. An airflow passing through the device 1 and through a cylindrically shaped consumable 41 (FIG. 3) or through a cuboidal shaped consumable 42 (FIG. 4) is shown.

The device housing 1 includes the receiving chamber 3, one consumable 41,42 accommodated in the respective part of the receiving chamber 3, a power source 22, for example a battery, and a controller 21 for controlling the power source 22 and the device.

The first-type consumable 41 is a heated liquid containing cartridge. An aerosol-forming liquid (or, alternatively referred to as a "pre-vapor formulation") is contained in a hollow tubular shaped reservoir. The reservoir may, for example, be filled with a high retention material. The liquid is supplied by a wick material to a coil heater 60, where the liquid is heated and evaporated. In a central conduit 401 of the first consumable 41, the evaporated liquid may be led out of the consumable 41. The cylinder part 31 of the receiving chamber 3 includes electrical contacts 61 for providing power from the power source 22 to the coil heater 60 of the first-type consumable 41. Corresponding electrical contacts 62 are provided at the distal end of the first-type consumable 41.

In FIG. 3 an airflow 50 enters the device 1 at a distal end of the device, passes through the device housing 2 and enters the distal end of the receiving chamber 3. The airflow 50 passes the receiving chamber 3 and passes through the central conduit 401 of the first-type consumable 41. Thereby the airflow 50 picks up evaporated substances, for example flavors or nicotine. The airflow 50 may then, for example, pass into a mouthpiece (not shown) aligned with the device housing 2.

The cuboidal part 32 of the receiving chamber 3 includes heating elements 63, which are indicated by black lines. The heating elements 63 are arranged in the lateral side portions of the cuboidal part 32 of the receiving chamber 3 for heating the rectangular block of tobacco material. The heating elements 63 are not arranged in the central cylindrical part 31 of the receiving chamber.

In an embodiment, with the first-type consumable 41 accommodated in the receiving chamber 3, the heating elements 63 are not supplied with power.

The second-type consumable 42, as depicted in FIG. 4, is a rectangular block of solid tobacco material, for example shredded tobacco or an homogenized tobacco material.

In FIG. 4 an airflow 50 entering the device at the distal end of the device passes through the device housing 2 and enters the distal end of the receiving chamber 3. The airflow 50 then passes the tobacco material of the second-type consumable 42. Thereby the airflow 50 picks up tobacco flavor and substances evaporated from the heated tobacco material. In an embodiment, with the second-type consumable accommodated in the receiving chamber 3, the electrical contacts 61 are not supplied with power.

FIG. 5 illustrates another consumable having the shape of the first-type consumable 41, accommodated in the cylindrical part of the receiving chamber 3 of the device 1, in accordance with an example embodiment. The electrical contacts 61 in the cylindrical part 31 of the receiving chamber are in contact with electrical contacts 62 of the consumable 41. The consumable 41 includes an aerosol-forming liquid in a storage portion 410 of the consumable 41. The storage portion 410 includes an open end, where a mesh heater 64 or other fluid permeable heater, is arranged over the open end. The liquid is heated by the heated mesh heater 64. The consumable is positioned in the receiving chamber 3 such that an airflow 50 entering the distal end of the receiving chamber 3 passes the mesh heater 64, picks up evaporated substances, then passes along the exterior of the consumable 41 before exiting the device housing 2 at the proximal end of the consumable 41.

Figure 6:
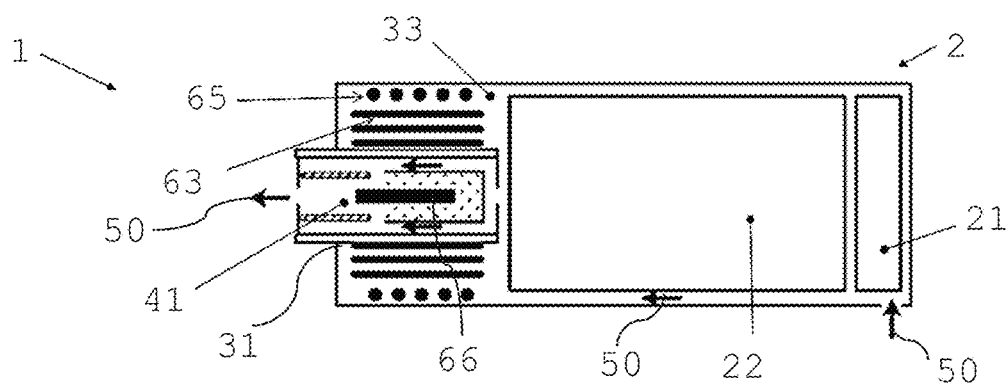
FIG. 6 illustrates a cross-sectional view of the devices shown in FIGS. 1 and 2, in accordance with an example embodiment.

FIG. 6 illustrates an alternative embodiment of the device 1 with induction heating for a first-type consumable 41 arranged in the cylindrical part 31 of the receiving chamber 3, in accordance with an example embodiment. The receiving chamber 3 is provided with heating elements 63 as shown, for example, in FIGS. 1 and 2, for heating a second-type consumable 42. In addition, in the receiving chamber side wall 33 an induction coil 65 is arranged. The induction coil 65 may surround the receiving chamber 3. Another type of consumable, in this example having the shape of a first-type consumable 41, is accommodated in the cylindrical part 31 of the receiving chamber 3. This type of consumable includes a susceptor 66, for example a ferrous material, for heating an aerosol-forming substrate in the consumable 41. The consumable 41 of FIG. 6 is depicted as containing liquid that is wicked and evaporated by the heated susceptor 66.

The induction heating is provided instead of electrical contacts 61 in the receiving chamber 3. However, electrical contacts 61,62 may be provided in addition to the induction heating to multiply the types of consumables being usable in the device of FIG. 6.

Figure 7:
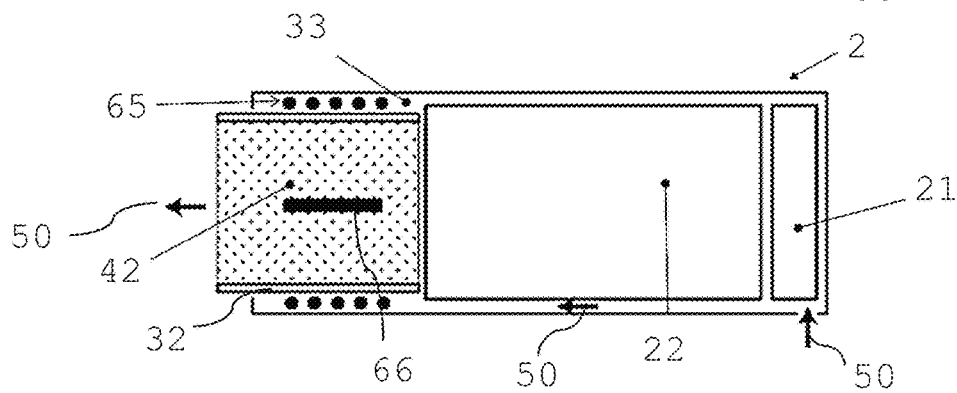
FIG. 7 illustrates a cross-sectional view of the devices shown in FIGS. 1 and 2, in accordance with an example embodiment.

FIG. 7 illustrates the device 1 including induction heating as in FIG. 6, in accordance with an example embodiment. A consumable in the form of a second-type consumable 42 is introduced in the cuboidal part 32 of the receiving chamber 3. The consumable 42 is a block of tobacco material including a susceptor 66 arranged in the tobacco material. Heating elements 60 as in FIG. 6 may be present, or not. The induction heating may be the only heating provided in the device.

The detection system in the device that may be integrated or connected to the controller 21 may recognize the type of consumable accommodated in the receiving chamber 3. For example, next to an electronic recognition, a touch sensor may be provided in the receiving chamber 3, for example in the cylindrical part 31 or in the cuboidal part 32 of the receiving chamber 3. Two touch sensors may be provided, one in the cylindrical part 31 and one in the cuboidal part 32 of the receiving chamber 3.

Figure 8:
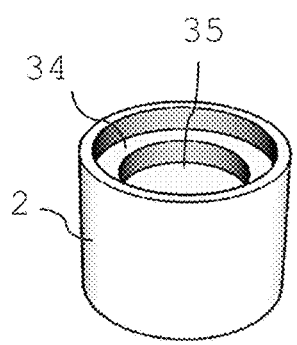
FIG. 8 illustrates structures in a bottom wall of a receiving chamber of a device, in accordance with an example embodiment.

FIG. 8 illustrates a bottom wall 34 of a receiving chamber 3, which is provided with a recess 35, in an example embodiment. The bottom wall 34 as well as recess 35 have a circular shape. The recess 35 is arranged symmetrically in the center of the bottom wall 34.

Figure 9:
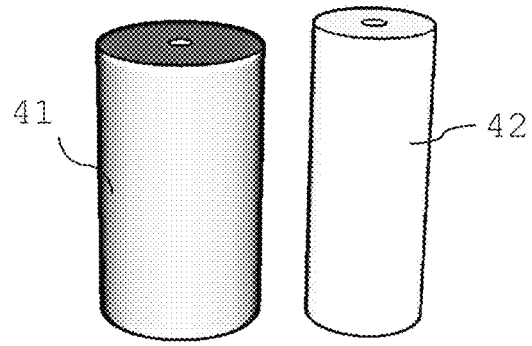
FIG. 9 illustrates consumables to be used with the structures of FIG. 8, in accordance with an example embodiment.

FIG. 9 illustrates two types of cylindrical consumables 41,42 adapted to be received in a receiving chamber 3 including the bottom wall 34 shown in FIG. 8, in an example embodiment. The consumable 42 having the smaller cross section is inserted into the recess 35 when accommodated in the receiving chamber 3. The consumable 41 having the larger cross section is in contact with the bottom wall 34 when accommodated in the receiving chamber 3. The consumables 41,42 of FIG. 9 are depicted as sealed containers, for example including an aerosol-forming liquid. The consumables 41,42 may however also be, for example, tubular housings filled with a tobacco material.

Figure 10:
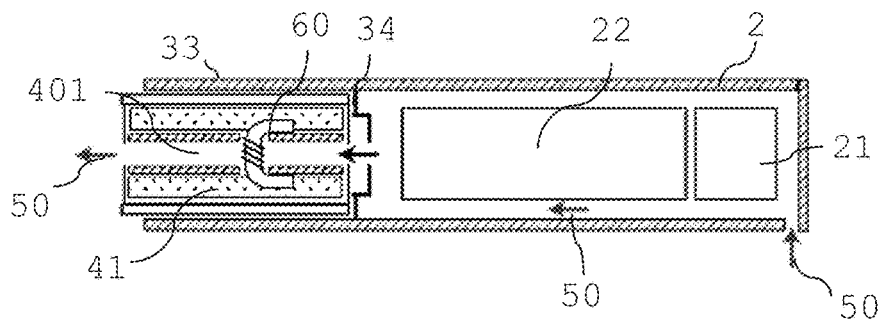
FIG. 10 illustrates a cross-sectional view of a device with the structures of FIG. 8 and the consumable of FIG. 9, in accordance with an example embodiment.
Figure 11:
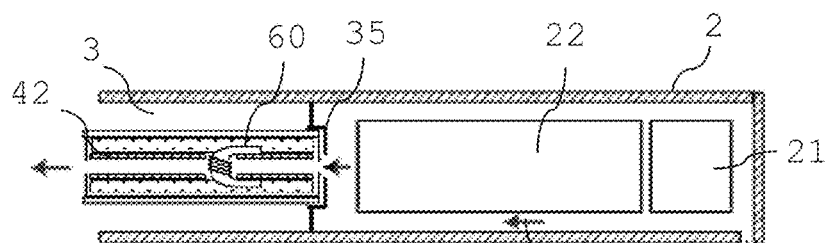
FIG. 11 illustrates a cross-sectional view of a device with the structures of FIG. 8 and the consumable of FIG. 9, in accordance with an example embodiment.

The consumable 42 to be arranged in the recess 35 is longer, in height, than the recess 35. By this, when accommodated in the receiving chamber 3, a proximal end of each consumable has a same level with respect to the outlet opening of the receiving chamber 3. This may also be seen in FIGS. 10-13. FIG. 10 and FIG. 11 illustrate examples of two same types of consumables, with a liquid containing cartridge, which liquid is supplied by a wick material to a coil heater 60, where the liquid is heated and evaporated. In a central conduit 401, the evaporated liquid may be led out of the consumable. The two consumables shown in FIGS. 10 and 11 differ in their size, in particular in their diameter and length. In an embodiment, the two cartridges differ, for example, in any one or a combination of strength of nicotine, flavor or aerosol volume.

The first-type consumable 41 shown in FIG. 10 is arranged flush with the receiving chamber side walls 33. The bottom wall 34 forms an end stop for the first-type consumable 41.

The second-type consumable 42 is only in contact with the recess 35. For further stability and stable position of the second-type consumable, the device 1 may be provided with a mouthpiece (not shown) including a recess corresponding to and receiving the proximal end of the second-type consumable 42.

Figure 12:
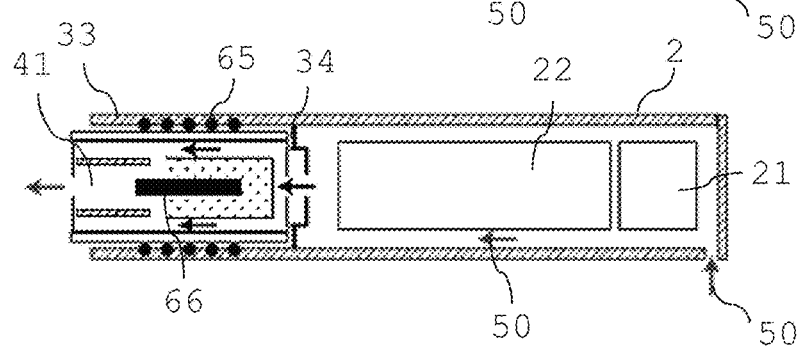
FIG. 12 illustrates a cross-sectional view of a device with the structures of FIG. 8 and the consumable of FIG. 9, in accordance with an example embodiment.
Figure 13:
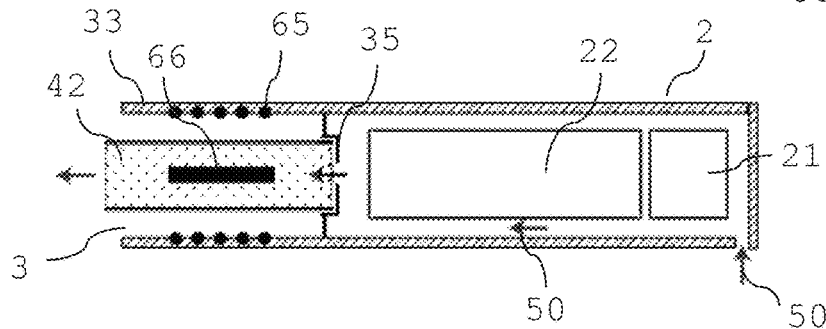
FIG. 13 illustrates a cross-sectional view of a device with the structures of FIG. 8 and the consumable of FIG. 9, in accordance with an example embodiment.

FIGS. 12 and 13 illustrate different first-type and second-type consumables 41,42 to be used in a device 1 including a receiving chamber bottom wall 34, as depicted in FIG. 8.

The first-type consumable 41 is depicted as inductively heatable liquid containing cartridge. The second-type consumable 42 is depicted as inductively heatable tobacco plug. Both consumables 41,42 include an elongated susceptor 66 arranged in the consumable.

The device includes an induction coil 65 arranged in the receiving chamber side wall 33 surrounding the receiving chamber 3.

Heating of the two types of consumable 41,42 may be identical. However, heating may be different and identified by consumable recognition according to the different structures the consumables 41,42 are received in.

Figure 14:
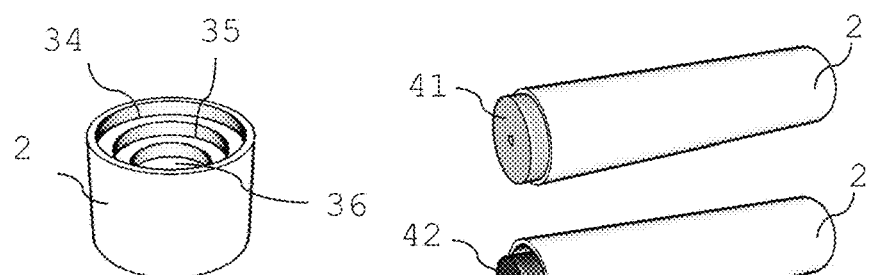
FIG. 14 illustrates structures in a bottom wall of a receiving chamber of a device, in accordance with an example embodiment.
Figure 15:
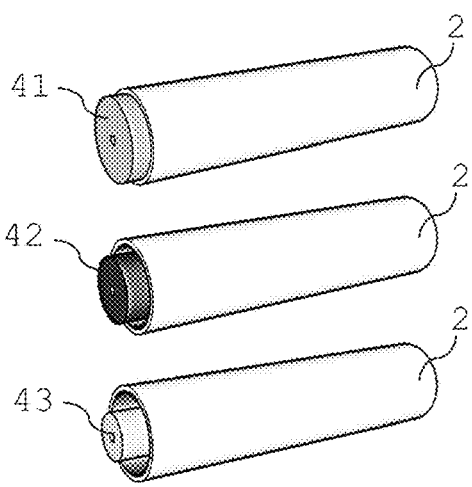
FIG. 15 illustrates consumables to be used with the structures of FIG. 14, in accordance with an example embodiment.

FIG. 14 depicts a bottom wall 34 of a receiving chamber, which is provided with two recesses 35,36, in an example embodiment. The bottom wall 34 as well as both recesses 35,36 have a circular shape. The recesses 35,36 are arranged symmetrically in the center of the bottom wall 34. The recesses 35,36 are arranged in a staggered manner such that the second recess 36 forms a recess of the first recess 35. FIG. 15 illustrates a device housing with three types of cylindrical consumables 41,42,43 accommodated in the respective recesses 35,36 of the bottom wall 34 of the receiving chamber.

The air gap between the consumables 41,42,43 and the receiving chamber side wall (non-existent gap, small gap, larger gap) may be used as an indicator for the type of consumable accommodated in the receiving chamber 3. In particular, when using induction heating, coupling of electromagnetic waves into a susceptor is dependent on the material between the susceptor and the inductor (air; gap size). Alternatively, if the consumables 41,42,43 include their own heating element, for example a resistively heatable heater, electrical contacts provided in the bottom wall 34 or in the respective recesses 35,36 of the receiving chamber may be used in a detection system of the device. A contact or non-contact with the electrical contacts in the receiving chamber may indicate if a consumable is present and in use or not in use.

FIGS. 16 and 17 schematically show a cylindrically shaped device housing 2 including a cylindrically shaped receiving chamber 3, in an example embodiment.

The receiving chamber side wall 33 includes a longitudinally arranged slit 37. A portion of the receiving chamber side wall 33 is partly replaced by a movable wall portion 70. The movable wall portion 70 is smaller than the missing portion of the side wall, which therefore defines a longitudinal slit 38, 39 in between the movable wall portion 70 and the remaining side wall. The movable wall portion 70 works as a structure selector. In FIG. 16, the structure selector is in a first position creating a longitudinal slit 38 at one side of the movable wall portion, only. The fixed slit 37 and the created slit 38 are arranged in the receiving chamber side wall at circumferential positions including an angle of less than 180 degree, for example about 120 degree. In FIG. 17, the structure selector, that is the movable wall portion 70, is in a second position defining another longitudinal slit 39 at the opposite side of the movable wall portion 70. The fixed slit 37 and the defined slit 39 are arranged directly opposite each other at circumferential positions including an angle of 180 degree.

FIG. 18 illustrates a first-type consumable 41 and a second type consumable 42 adapted to correspond to the receiving chamber of FIGS. 16 and 17, in an example embodiment. The consumables 41,42 each include two radially extending ribs 411 at the circumference of the proximal end of the consumable. The ribs extend over about half of the length of the consumables. The ribs 411 of the first consumable 41 are positioned on the circumference of the consumable, where the ribs may be at an angle of about 120 degrees apart. The ribs 411 of the second consumable 41 are positioned on the circumference of the consumable opposite, at may be at an angle of about 180 degrees apart.

The different shapes of the consumable and corresponding shapes of the device allows the consumables to be correctly identified.

As shown in FIGS. 19 and 20, the consumables are inserted into the receiving chamber 3. The ribs 411 are guided along the slits 37,38,39 and received therein when the consumables 41,42 are accommodated in the receiving chamber. The ribs 411 have a size (tolerance) that provides a close fit within the slits, where the ribs 411 are flush with the outer circumference of the device housing 2. In these embodiments, a proximal end of the consumables 41, 42 is also flush with the proximal end of the device housing when the consumables are arranged in the housing 2.

In FIG. 19 the structure selector is positioned in the second position such as to only allow second-type consumables 42 to be accommodated in the receiving chamber 3, in an example embodiment. Accordingly, in FIG. 20 the structure selector is positioned in the first position such as to only allow first-type consumables 41 to be accommodated in the receiving chamber 3.

The position of the movable wall portion 70 may directly be correlated to an operation mode of the device for operating only the respective consumable.

Figure 21:
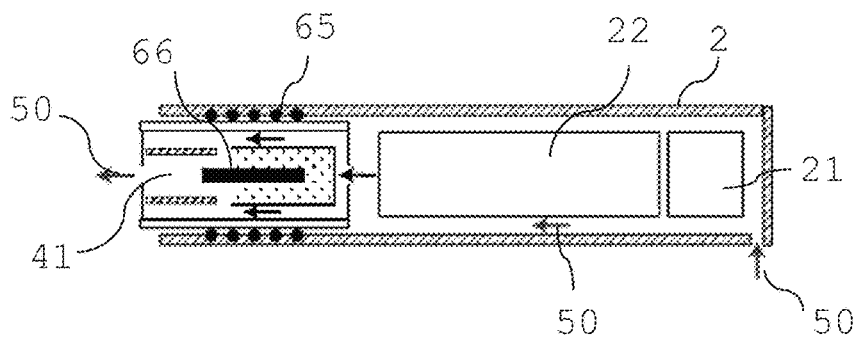
FIG. 21 illustrates cross-sectional views of a device, in accordance with an example embodiment.
Figure 22:
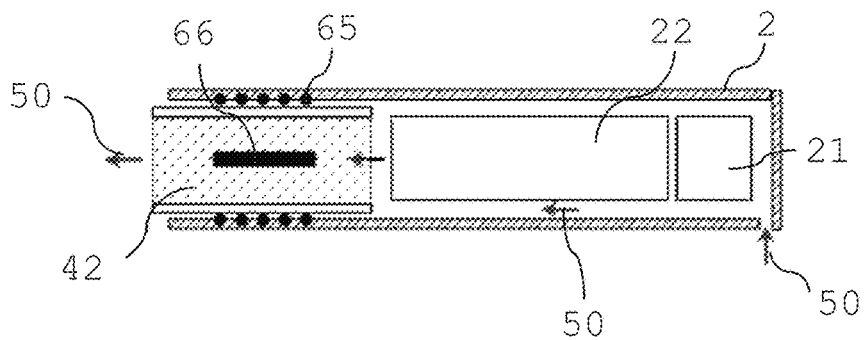
FIG. 22 illustrates cross-sectional views of a device, in accordance with an example embodiment.

FIGS. 21 and 22 illustrate examples of device with a structure selector in the form of a movable wall portion (not visible), in an example embodiment. FIG. 21 depicts the device with the structure selector in the first position and FIG. 22 depicts the device with the structure selector in the second position.

The device is provided with an induction coil 65 extending around the circumference of the receiving chamber 3.

The first-type consumable 41 is a liquid including a cartridge with a susceptor 66. The structure selector in the first position accepts this first-type consumable 41 with corresponding ribs 411, only. With the structure selector being in the first position, the device may be set to use the first-type consumables 41, only.

The second-type consumable 42 of FIG. 22 is a plug of tobacco material including a susceptor. The consumable 42 fits into the device with the structure selector in the second position. The device recognizes the correct consumable 42 and will activate the induction coil 65.

For a consumable recognition and individual heating of a consumable, a consumable may be provided with independent electrical contacts if the consumable includes an internal heater. The electrical contacts may be used in a resistance circuit of the device, where the device determines the presence and type of consumable accommodated in the receiving chamber. Another consumable recognition may be a switch that is manually operated. The switch is set according to a consumable that is inserted into the device. Different consumable recognition modes may be used individually or in combination in a detection system of the device.

Figure 23:
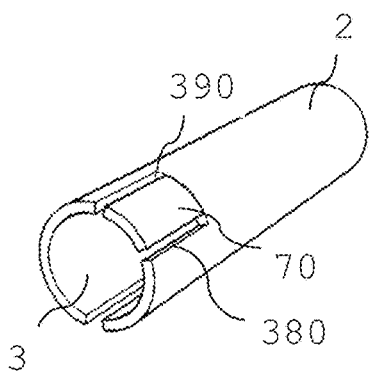
FIG. 23 illustrates a structure selector, in accordance with an example embodiment.

FIG. 23 schematically shows a cylindrically shaped device housing including a cylindrically shaped receiving chamber 3, in an example embodiment. The receiving chamber side wall 33 includes a longitudinally arranged slit 37.

A portion of the receiving chamber side wall 33 is partly replaced by a movable wall portion 70. The movable wall portion is smaller than the missing portion of the side wall, as shown in FIGS. 16 and 17. In FIG. 23, the movable wall portion 70 is in a third position, which define two longitudinal slits 380, 390 on each side of the wall portion in between the movable wall portion 70 and the remaining side wall 33. The slits 380,390 created with the movable wall portion 70 in the third position are smaller than the slits 38,39 when the movable wall portion 70 is in the first or second position.

The fixed slit 37 and one of the defined slits 380 are arranged in the receiving chamber side wall at circumferential positions including an angle of about 120 degrees. The other one of the created slits 390 is arranged directly opposite the fixed slit 37 at circumferential positions including an angle of about 180 degrees. This device may be used in combination with the two consumables shown in FIG. 18 (with the movable wall portion 70 in the respective first or second position) as well as with the consumable shown in FIG. 24.

Figure 24:
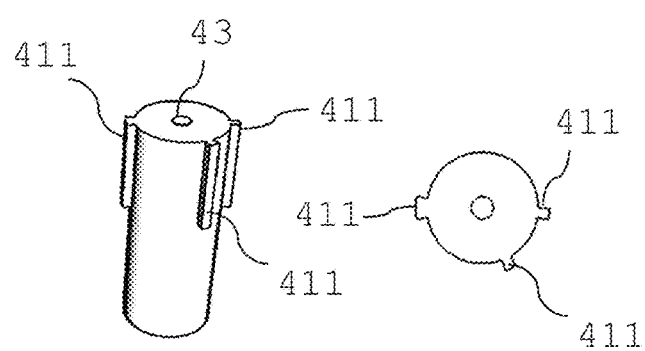
FIG. 24 illustrates a third consumable, in accordance with an example embodiment.

FIG. 24 illustrates a third-type consumable 43 adapted to correspond to the receiving chamber as shown in FIG. 23, in an example embodiment. The third-type consumable 43 includes three radially extending ribs 411 at the circumference of the proximal end of the consumable. The ribs extend over about half of the length of the consumable. The ribs 411 of the third-type consumable 43 are positioned on the circumference of consumable including an angle of about 120 degree and 180 degree.

Figure 25:
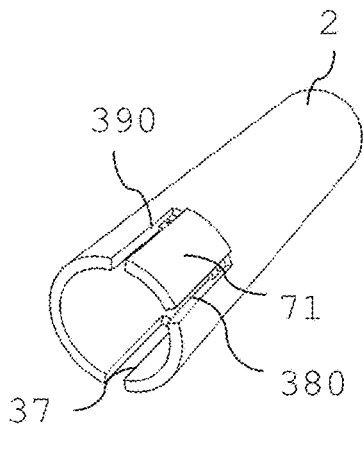
FIG. 25 illustrates a removable structure selector in a mounted position, in accordance with an example embodiment.
Figure 26:
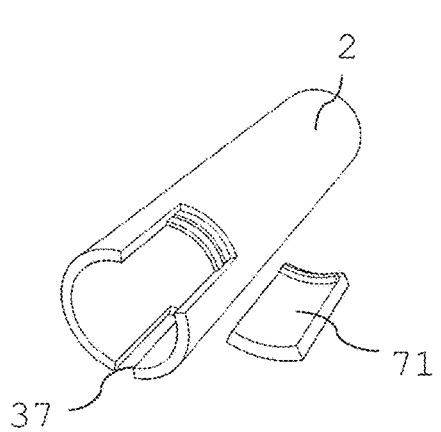
FIG. 26 illustrates a removable structure selector in a removed position, in accordance with an example embodiment.

FIGS. 25 and 26 illustrate a structure selector in the form of a removable wall portion 71, in an example embodiment. In these example embodiments, the removable wall portion is also a movable wall portion, as shown in the examples of FIGS. 16, 17 and 25. The removable wall portion 71 may be positioned in three positions when mounted in the receiving chamber side wall: one first position on an extreme left side, a second position to an extreme right side and a third position in the middle between the extreme left and extreme right side. When the removable wall portion 71 is removed, as shown in FIG. 26, this corresponds to a disabled receiving chamber and a disabled device, accordingly. A controller of the device may be connected to the removable wall portion 71 to receive the respective information on a mounted or on a removed wall portion 71.

Figure 27:
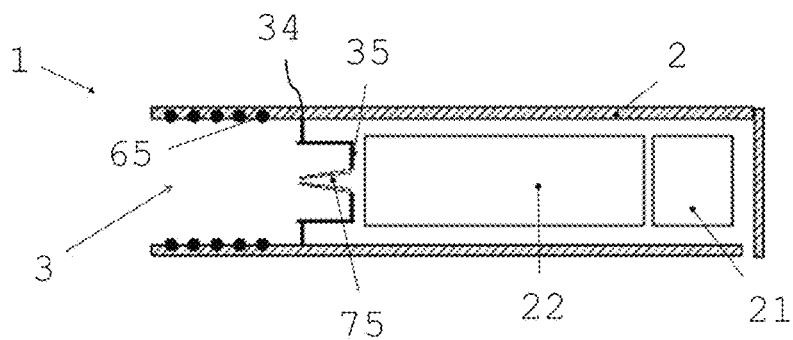
FIG. 27 illustrates a cross-sectional view of a device including a piecing member, in accordance with an example embodiment.

In FIG. 27, a further embodiment of an aerosol-generating device is illustrated, in an example embodiment. The receiving chamber 3 includes a recess 35 in the bottom wall 34 of the receiving chamber 3. A puncturing member 75 in the form of a pointed pin is arranged in the recess 35. The puncturing member 75 points into the direction of the receiving chamber 3 and has a height corresponding to the height of the recess 35.

The piercing member 75 is open to allow an airflow through the piercing member into the receiving chamber, or rather into a consumable pierced by the piercing member 75.

The device 1 includes an induction coil 65 for inductively heating aerosol-forming substrate in consumables accommodated in the receiving chamber 3.

Figure 28:
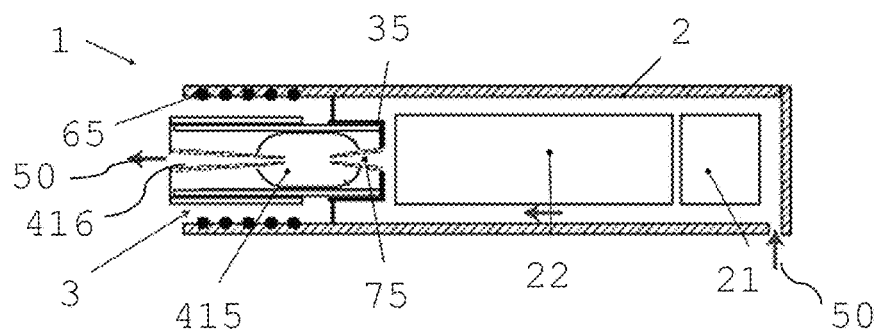
FIG. 28 illustrates cross-sectional views of the device of FIG. 27 in combination with consumables, in accordance with an example embodiment.
Figure 29:
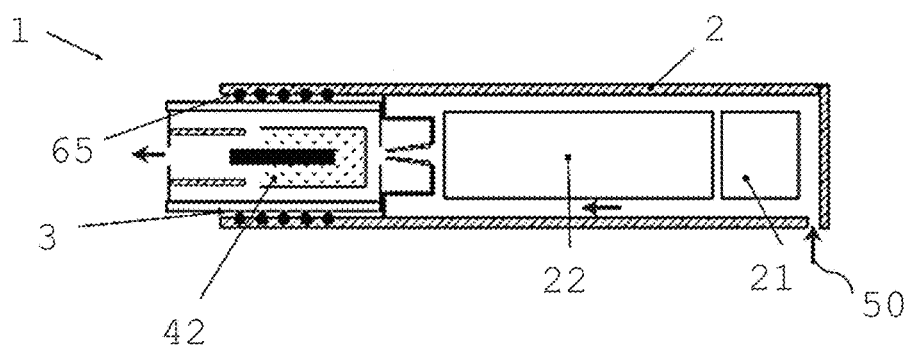
FIG. 29 illustrates cross-sectional views of the device of FIG. 27 in combination with consumables, in accordance with an example embodiment.
Figure 30:
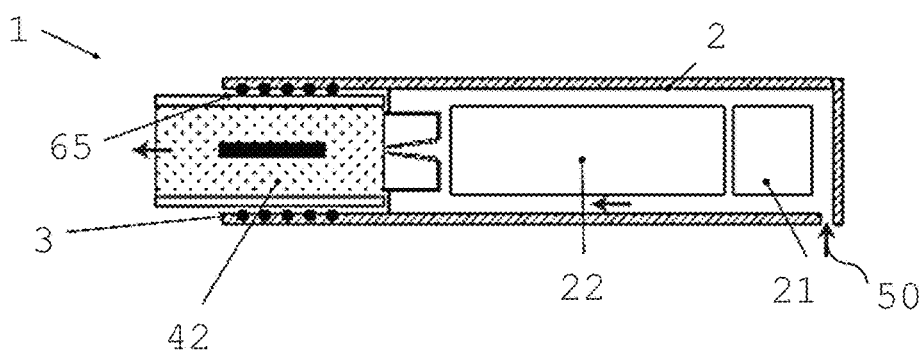
FIG. 30 illustrates cross-sectional views of the device of FIG. 27 in combination with consumables, in accordance with an example embodiment.

FIGS. 28, 29 and 30 illustrate different types of consumables to be used in the device of FIG. 27, in an example embodiment.

In FIG. 28, a first-type consumable, which includes a dry powder, is accommodated in the device. The consumable includes a capsule 415 with the powder. The capsule 415 is pierced on one longitudinal side by a first piercing member 416. The first piercing member 416 may be part of the consumable or, for example, part of a mouthpiece. In an embodiment, the first piercing member 416 is open to allow a content of the capsule 415 to leave the capsule 415 through the first piercing member 416. The opposite side of the capsule 415 is pierced by the piercing member 75 of the device when the capsule 415 is accommodated in the recess 35 of the receiving chamber 3. Through the piercing of the capsule an airflow passageway is created through the capsule 415 allowing the powder to be carried out of the capsule with the airflow 50. This first-type consumable does not require heating.

In FIGS. 29 and 30, a second-type of consumables 42 are depicted that may be used in the device of FIG. 27, in an example embodiment. The second-type of consumables 42 have a cross section that is the size of the cross section of the receiving chamber 3. The consumables 42 do not extend into the recess 35 and are unaffected by the puncturing member 75. Both second-type of consumables 42 include a susceptor and may inductively be heated. The second-type consumable 42 of FIG. 29 is depicted as a heatable liquid containing reservoir. The second-type consumable 42 of FIG. 30 is depicted as a heatable tobacco substrate. The open piercing member 75 allows an airflow to enter the receiving chamber 3 through the piercing member and through the second-type consumables 42.

Figure 31:
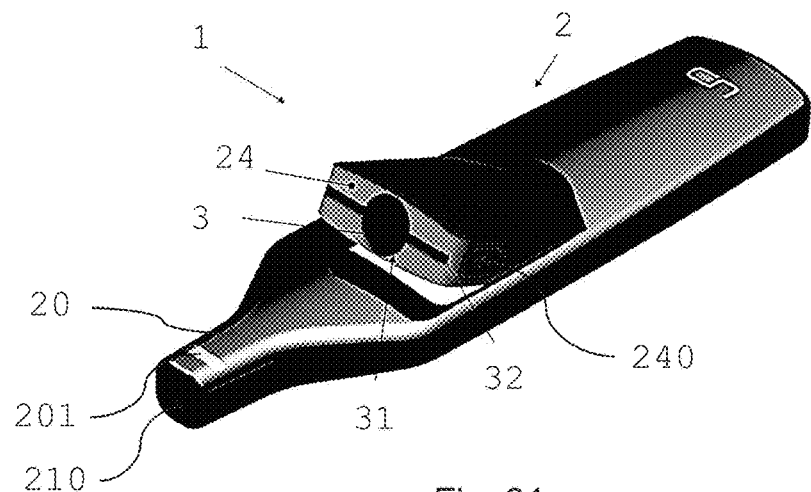
FIG. 31 illustrates a perspective view of a device with a hinged portion, in accordance with an example embodiment.

FIG. 31 illustrates a device with a device housing 2 with an integrated mouthpiece 20. The device housing 2 includes a hinged housing portion 24, in an example embodiment. The receiving chamber 3 for receiving a first-type consumable or a second type consumable is arranged in the hinged housing portion 24. The hinged housing portion 24 may be tilted along a hinge (not shown) in the device housing. In a closed position of the hinged housing portion 24, the housing portion 24 is aligned with the entire housing 2 and the receiving chamber 3 is not accessible. In an open configuration of the hinged housing portion 24, as shown in FIG. 31, the hinged housing portion 24 is tilted out of the plane of the device housing 2 and the receiving chamber 3 is accessible. In the illustrated embodiment, the receiving chamber 3 has the form of a hollow cylinder 31 combined with a hollow cuboid 32.

The hinged housing portion 24 may include an eject button 240 for activating an ejection mechanism for a consumable accommodated in the receiving chamber 3.

The mouthpiece 20 may be provided with a lip sensor 201 in the region of the outlet 210 of the mouthpiece. The lip sensor 201 may be designed such that the system recognizes a ready to use state of the device 1.

Figure 32:
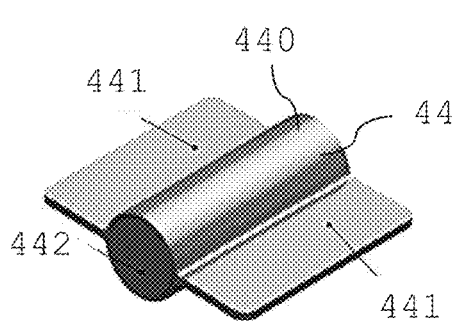
FIG. 32 illustrates a consumable insert to be used in the device of FIG. 31, in accordance with an example embodiment.

FIG. 32 illustrates a consumable insert 44 suitable for being inserted into the receiving chamber 3 of the device 1 of FIG. 31, in an example embodiment. The consumable insert 44 includes a cylindrical portion 440, which is filled with a solid tobacco substrate 442. The consumable insert 44 includes two flaps 441 depending from the cylindrical portion 440. The flaps 441 are arranged at opposite sides of the cylindrical portion 440.

The flaps serve for a specific positioning of the consumable insert 44 in a receiving chamber, for example to allow a precise positioning of an inductor in the device and a susceptor in the consumable insert 44.

In one embodiment, the flaps 440 do not include an aerosol-forming substrate or powder.

In another embodiment, the flaps 440 include a liquid aerosol-forming substrate. The consumable insert 44 then forms a hybrid consumable, wherein a tobacco substrate 442 as well as a liquid aerosol-forming substrate is made available by the one consumable insert 44.

Figure 33:
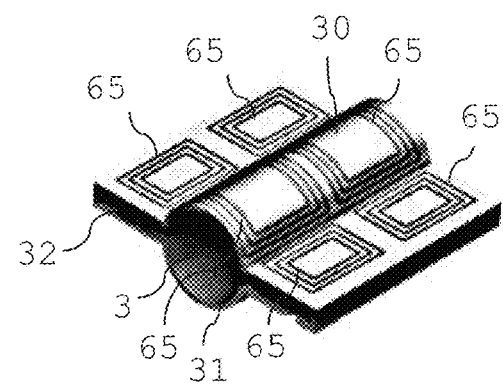
FIG. 33 illustrates a heating set-up for a receiving chamber of the device of FIG. 31, in accordance with an example embodiment.

FIG. 33 illustrates a housing portion insert 30 depicting an example of inductive heating of consumables inserted into the receiving chamber 3 having the shape, as shown and described in the device of FIG. 31, in an example embodiment. On the external wall of the housing portion insert 30, an induction coil is split axially and radially and forms an arrangement of induction coils 65. Two split coils 65 are each arranged on the cylindrical portion 31 and on the cuboid portion 32. In an embodiment, the coil arrangement is symmetric on both sides of the housing portion insert 30. In an embodiment, the individual induction coils 65 may be activated at appropriate frequencies in a continuous or pulsed power mode to inductively power any type of inductively activatable consumable accommodated in the receiving chamber 3.

Figure 34:
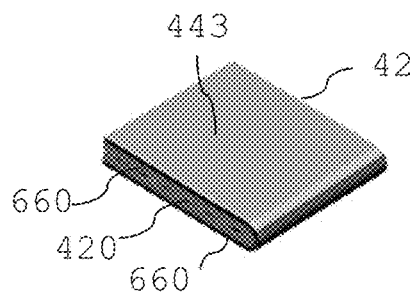
FIG. 34 illustrates another embodiment of a consumable to be used, for example, in the device of FIG. 31, in accordance with an example embodiment.

FIG. 34 illustrates a second-type consumable 42 having a cuboidal form, in accordance with an example embodiment. The composite consumable includes an insulator layer 420 and a susceptor layer 660 above and below the insulator layer 420. The susceptor layers 660 are covered by a tobacco layer 443. The susceptor layers 660 on each side of the insulator layer 420 may be independently activated. Accordingly the insulator is non-transparent for electromagnetic waves of an inductor. In an embodiment, the insulator layer 420 is also thermally insulating such as to not transport heat generated in the susceptor layer on one side of the insulator layer 420 to the other side of the insulator layer.

Such a composite consumable may, for example, be manufactured by providing a tobacco layer 443, a split susceptor material layer 660 and an insulator layer 420 on top of each other. The so formed stack may be folded such that the insulator layer 420 comes to lie on itself.

This second-type consumable 42 may be inserted into the cuboid part 32 of the receiving chamber 3 of the device 1 depicted in FIG. 31, provided that the device includes an inductive heating structure.

Figure 35:
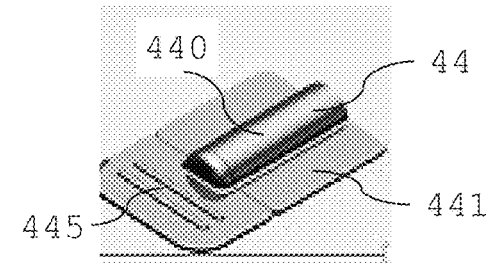
FIG. 35 illustrates a sealing structure for the consumable of FIG. 32, in accordance with an example embodiment.

In FIG. 35 the consumable insert 44 of FIG. 32 is depicted to include a break-off tab 445. The tab 445 seals the opening of the cylindrical portion 440 of the inset 44 and protects the tobacco material 442 in the consumable insert 44 until use of the consumable. The break-off tab 445 has to be broken away before use of the consumable insert.

In case the flaps 441 serve as a liquid aerosol-forming substrate reservoir, the break-off tab also seals the opening of the flaps 441.

Figure 36:
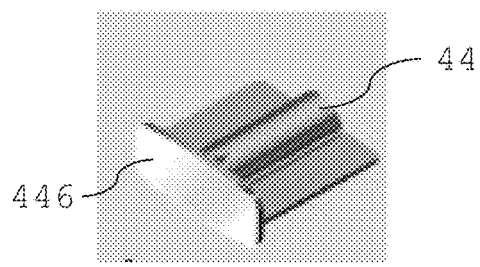
FIG. 36 illustrates a sealing structure for the consumable of FIG. 32, in accordance with an example embodiment.

In FIG. 36, the consumable insert 44 of FIG. 32 is depicted to include a sealing foil 446. The sealing foil 446 seals the opening of the cylindrical portion 440, and optionally also covers the flaps 441. The sealing foil 446 protects the tobacco material 442 in the consumable insert 44, and if present the sealing foil 446 also protects the liquid substrate, until use of the consumable. The sealing foil 446 is removed before use of the consumable insert.

Figure 37:
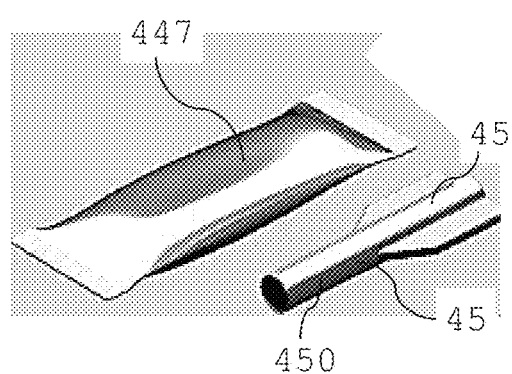
FIG. 37 illustrates a further sealing structure for the consumables of FIGS. 32, 34 and 35, in accordance with an example embodiment.

Additional protection of a consumable, or a consumable insert, for example the protection of the embodiment shown in FIG. 32, may be accomplished using a sealed sachet 447 as depicted in FIG. 37. The sachet 447 seals a consumable within an environment that may be a gas-tight and chemically inert sachet material.

Next to the sachet 447, another hybrid consumable insert is depicted. The consumable insert 45 has the form of a rocket. The distal portion 451 having a cylindrical portion and flaps includes tobacco material or an aerosol-forming substrate to be vaporized. The distal portion 451 is inserted into a respectively shaped receiving chamber of a device for heating the substrate in the insert 45. The proximal portion 450 of the consumable insert 45 is an extended cylindrical portion. The proximal portion 450 serves as a mouthpiece. With this consumable insert 45, a new mouthpiece is used each time a consumable is replaced. By this, contamination of the device with different tobacco substrates may be avoided. In addition, cleaning of the device may be omitted or limited.

What is claimed is:

1. An e-vaping device, comprising:
a first housing; and
a chamber defined within the first housing, the chamber defining a first-shaped cavity and a second-shaped cavity, the first-shaped cavity being configured to receive one first-type consumable within the chamber and the second-shaped cavity being configured to receive one second-type consumable within the chamber.

2. An e-vaping device, comprising:
a first housing; and
a chamber defined within the first housing, the chamber defining a first-shaped cavity and a second-shaped cavity, the first-shaped cavity being configured to receive one first-type consumable within the chamber and the second-shaped cavity being configured to receive one second-type consumable within the chamber, the chamber being configured to prevent an insertion of more than one consumable into the chamber at a time.

3. The e-vaping device of claim 1, wherein
the first-shaped cavity and the second-shaped cavity being positioned within the chamber, and
the first-shaped cavity and the second-shaped cavity differing in at least one of a shape, a size and a position.

4. The e-vaping device of claim 1, wherein the first-shaped cavity includes a first-type recess defined by an end-wall of the chamber and the second-shaped cavity includes a second-type recess defined by the end-wall.

5. The e-vaping device of claim 1, wherein the first-shaped cavity and the second-shaped cavity include slits that are at least one of defined in the first housing, defined in an interior wall of the chamber, or combinations thereof.

6. The e-vaping device of claim 1, wherein
the first-shaped cavity partially overlaps with the second-shaped cavity.

7. The e-vaping device of claim 6, wherein the first-shaped cavity is a cuboidal shape and the second-shaped cavity is a cylindrical shape.

8. The e-vaping device of claim 1, further comprising:
a structure selector configured to select between the first-shaped cavity and the second-shaped cavity.

9. The e-vaping device of claim 8, wherein
the structural selector is a removable wall on an interior wall of the chamber, and
the structural selector is configured to slide between a first position and a second position.

10. The e-vaping device of claim 9, wherein the removable wall is configured to cause the e-vaping device to become disabled once the removable wall is removed from the interior wall.

11. The e-vaping device of claim 1, further comprising:
a power source; and
a controller operatively connected to the power source.

12. The e-vaping device of claim 11, further comprising:
a detection system configured to detect the one first-type consumable or the one second-type consumable within the chamber,
wherein the controller is configured to cause the e-vaping device to generate a vapor based on the detection system detecting the one first-type consumable or the one second-type consumable.

13. The e-vaping device of claim 11, further comprising:
at least one first heating element, the at least one first heating element being configured to interface with the one first-type consumable or the one second-type consumable within the chamber, the controller being operatively connected to the at least one first heating element.

14. The e-vaping device of claim 1, further comprising:
a cartridge, the cartridge being at least partially contained within the chamber, the cartridge being one of the one first-type consumable and the one second-type consumable.

15. The e-vaping device of claim 14, further comprising:
at least one heating element, the at least one heating element being in the cartridge.

16. The e-vaping device of claim 1, further comprising:
a consumable housing, the consumable housing being at least partially contained within the chamber, the consumable housing including one of the one first-type consumable or the one second-type consumable, the consumable housing including a mating structure that is conformed to a shape of one of the first-shaped cavity or the second-shaped cavity, respectively.

17. The e-vaping device of claim 16, wherein the mating structure is one of a shape of the consumable housing, at least one rib, an extension piece, a lug, at least one flap, or combinations thereof.

18. The e-vaping device of claim 1, wherein the chamber includes a third structure for receiving a third-type consumable, the third structure differing in at least one of a shape, a size and a position as compared to the first-shaped cavity and the second-shaped cavity.

19. An e-vaping device, comprising:
a first housing; and
a chamber defined within the first housing, the chamber defining a first-shaped cavity and a second-shaped cavity, the first-shaped cavity being configured to receive one first-type consumable within the chamber and the second-shaped cavity being configured to receive one second-type consumable within the chamber, the first-shaped cavity including a first annular recess defined by an end-wall of the chamber and the second-shaped cavity including a second annular recess defined by the end-wall, the second annular recess being concentrically positioned within the first annular recess.

20. An e-vaping device, comprising:
  a first housing; and
  a chamber defined within the first housing, the chamber defining a first-shaped cavity and a second-shaped cavity, the first-shaped cavity being configured to receive one first-type consumable within the chamber and the second-shaped cavity being configured to receive one second-type consumable within the chamber; and
  a structure selector configured to select between the first-shaped cavity and the second-shaped cavity, the structural selector including a movable wall on an interior wall of the chamber, the movable wall being configured to slide between a first position and a second position.

21. The e-vaping device of claim 20, wherein the first position exposes a first slit in the interior wall and the second position exposes a second slit in the interior wall, the first slit being defined by the first-shaped cavity and the second slit being defined by the second-shaped cavity.

* * * * *